(12) United States Patent
Lantz et al.

(10) Patent No.: US 8,422,633 B2
(45) Date of Patent: Apr. 16, 2013

(54) X-RAY BEAM DEVICE

(75) Inventors: Blandine Lantz, Saint Nizier'du Moucherotte (FR); Peter Hoghoj, St. Martin-le-Vinoux (FR)

(73) Assignee: Xenocs S.A., Sassenage (FR)

( * ) Notice: Subject to any disclaimer, the term of this patent is extended or adjusted under 35 U.S.C. 154(b) by 387 days.

(21) Appl. No.: 12/810,381

(22) PCT Filed: Jan. 2, 2009

(86) PCT No.: PCT/EP2009/050001
§ 371 (c)(1),
(2), (4) Date: Jun. 24, 2010

(87) PCT Pub. No.: WO2009/083605
PCT Pub. Date: Jul. 9, 2009

(65) Prior Publication Data
US 2010/0272239 A1    Oct. 28, 2010

(30) Foreign Application Priority Data
Dec. 31, 2007    (EP) .................................. 07291646

(51) Int. Cl.
*G21K 1/06* (2006.01)
(52) U.S. Cl.
USPC .............................................. 378/84; 378/85
(58) Field of Classification Search ............ 378/84, 378/85
See application file for complete search history.

(56) References Cited

U.S. PATENT DOCUMENTS

| | | | | |
|---|---|---|---|---|
| 3,032,656 A | * | 5/1962 | Hosemann et al. | 378/84 |
| 5,850,425 A | * | 12/1998 | Wilkins | 378/85 |
| 6,278,764 B1 | * | 8/2001 | Barbee et al. | 378/84 |
| 6,529,578 B1 | * | 3/2003 | Taguchi et al. | 378/84 |
| 2002/0003859 A1 | * | 1/2002 | Kogan | 378/84 |
| 2002/0027972 A1 | * | 3/2002 | Joy et al. | 378/85 |
| 2002/0136354 A1 | * | 9/2002 | Takenaka et al. | 378/84 |
| 2006/0018429 A1 | * | 1/2006 | Hoghoj et al. | 378/84 |

FOREIGN PATENT DOCUMENTS

FR    2850171    7/2004

OTHER PUBLICATIONS

Danhong Li, et al., "Source-optic-crystal optimization for compact monochromatic imaging" Proceedings of the SPIE—The Internationalsociety for Optical Engineering SPIE-Int. Soc.Opt. Eng USA, vol. 5537, No. 1, 2004, pp. 105-114, XP 002485423.

* cited by examiner

*Primary Examiner* — Glen Kao
(74) *Attorney, Agent, or Firm* — Notaro, Michalos & Zaccaria P.C.

(57) ABSTRACT

The invention refers to an X-ray beam device for X-ray analytical applications, comprising an X-ray source designed such as to emit a divergent beam of X-rays; and an optical assembly designed such as to focus said beam onto a focal spot, wherein said optical assembly comprises a first reflecting optical element, a monochromator device and a second reflecting optical element sequentially arranged between said source and said focal spot, wherein said first optical element is designed such as to collimate said beam in two dimensions towards said monochromator device, and wherein said second optical element is designed such as to focus the beam coming from said monochromator device in two dimensions onto said focal spot.

15 Claims, 7 Drawing Sheets

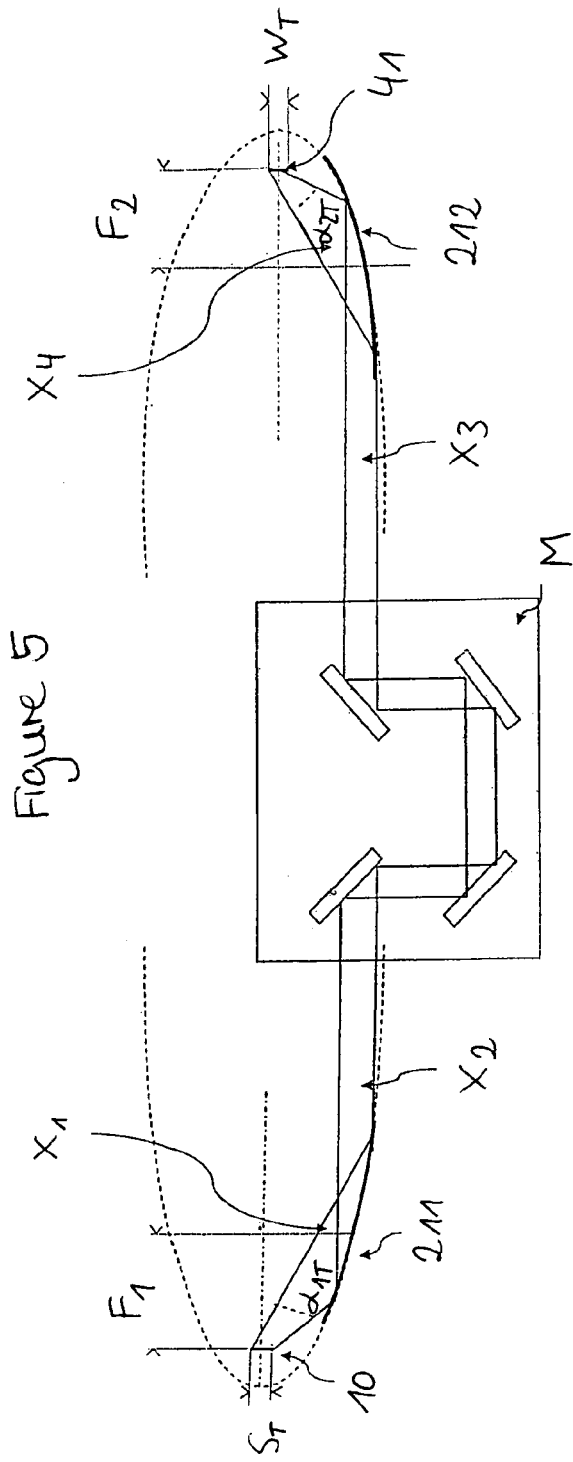

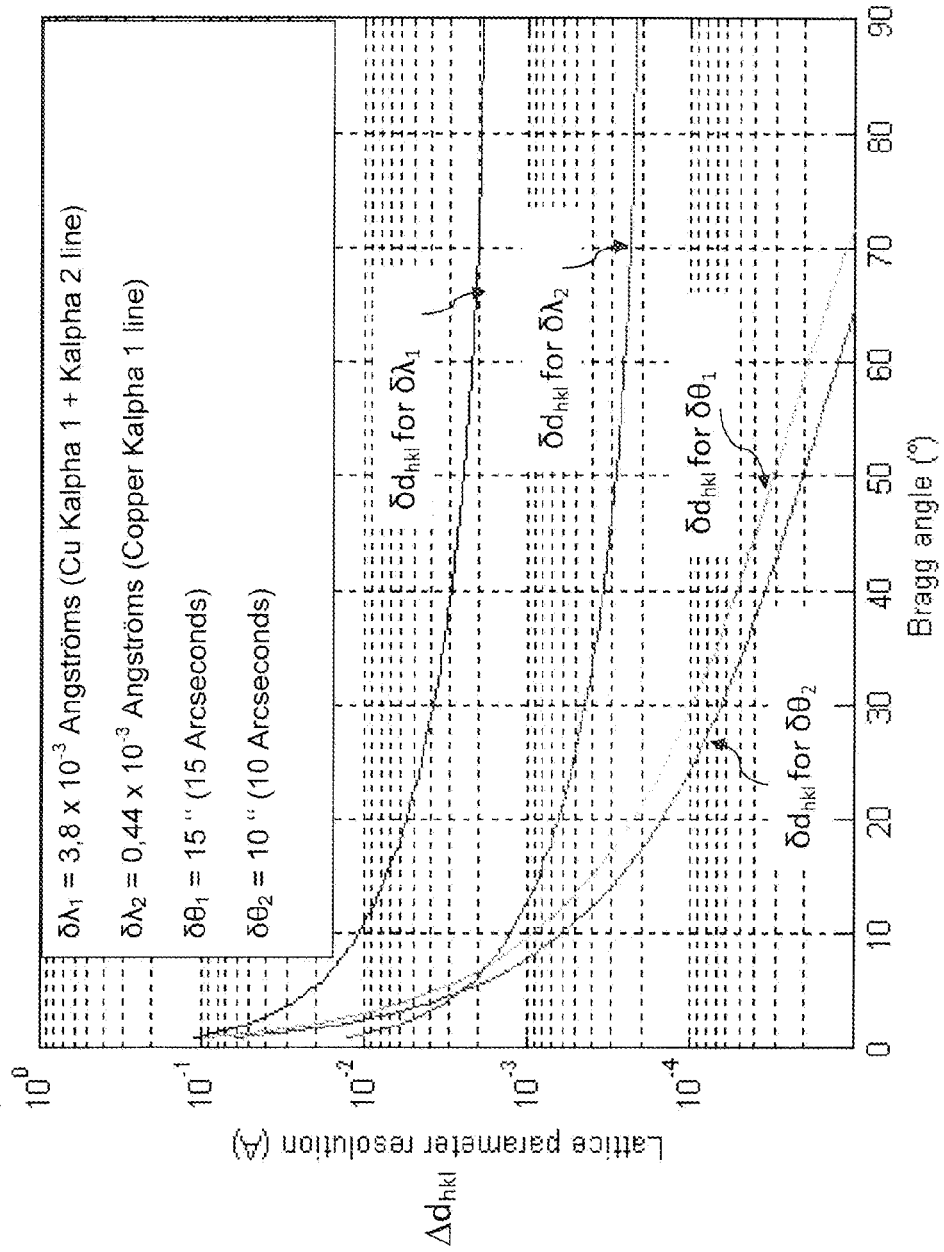

Ellipsoidal mirror for symmetric
focal distances F1= F2= 200 mm
Angle of incidence : 1.16°
Mirror length of 60mm
β=180°
Image at 300 mm from focal point F1=F2=200mm for the double
paraboloid optical assembly
Angle of incidence : 1.16° on each
mirror
Each mirror length : 60mm
β=180° for each mirror
Image at 300 mm from focal point

X-RAY BEAM DEVICE

BACKGROUND AND SUMMARY

The present invention relates to an X-ray beam device for X-ray analytical applications such as X-ray Diffractometry, High Resolution X-Ray Diffractometry, X-ray Reflectometry comprising an X-ray Source, typically a point focus X-ray source, and an x-ray focusing optical assembly for focusing monochromatic x-rays on a sample.

The invention will be more particularly adapted for High Resolution X-ray Diffraction applications. High Resolution X-ray Diffraction is a well established technique for carrying out the analysis of high quality thin layer of near perfect single crystals materials.

High resolution diffraction analysis requires to illuminate the sample with an X-ray beam having a very small divergence and a high energetic resolution. This is necessary to determine the parameters such as lattice spacing with a sufficient precision. Typically for High Resolution X-ray Diffraction applications in the case where Copper radiation is used, the energy resolution required is such that the incident x-ray beam needs to be filtered so that only $K\alpha 1$ line is transmitted to the sample. The $K\alpha 2$ line from the Copper $K\alpha$ doublet has consequently to be filtered.

The X-ray Beam Device according to the invention typically comprises a high brilliance X-ray source which can be either a sealed tube X-ray source or a rotating anode X-ray source with a point focus geometry. Laboratory X-ray sources have isotropic radiations and the characteristic X-ray spectrum emitted by an X-ray source with a Copper target is composed of several parasitic X-ray peaks and bremsstrahlung x-rays. Moreover the $K\alpha 1$ and $K\alpha 2$ lines are merged in the $K\alpha$ doublet.

X-ray multilayer optical elements composed of a Bragg reflective structure can be used to collect the beam emitted by an x-ray source in order to monochromatize and adapt the x-ray beam in real space and in angular space toward a sample. However the use of a multilayer optical element to filter the X-ray beam emitted by a source will be unsufficient for high resolution diffraction applications as for Copper X-ray beam radiation the $K\alpha 1$ and $K\alpha 2$ lines are merged after the reflection on the multilayer optical element.

Natural crystals (e.g. Si, Ge, LiF) can be used as X-ray optical elements in order to monochromatize an x-ray beam to the level of energetic resolution required for High Resolution X-ray Diffraction. However the efficiency of such natural crystals is limited when curved crystal elements necessary for focusing the X-ray beam emitted from the source are used (curvature deteriorates the very small lattice spacing structure). Such natural crystals typically have a corresponding angular acceptance of 10 to 30 Arcseconds. FIG. 1 is a schematic graph illustrating an example of angular acceptance $\Delta\theta_M$ of a crystal monochromator in terms of reflectivity.

One optical system arrangement typically used for high resolution x-ray diffraction applications is composed of an x-ray multilayer conditioning optic that is used to convert the divergent X-ray beam emitted by the X-ray source into a parallel beam before entering a crystal monochromator arranged downstream the multilayer optic. Such multilayer conditioning optic will be referred to a collimating optic in the description of the invention. The collimating effect of a multilayer conditioning optic is referring to the optical effect where a divergent beam collected by the optic is converted in a substantially parallel beam having a divergence lower than 1 milliradians typically.

FIG. 2 is illustrating a type of multilayer conditioning optic 20 producing a collimating effect wherein the optical element comprises a reflective surface being shaped according to two curvatures Cx and Cy corresponding to two different directions which are the sagittal direction (direction Y in FIG. 2) and the meridional direction (direction X in FIG. 2). These directions that will be referred to in the description of the invention can be defined with respect to the general direction of propagation of the X-ray beam:—the meridional direction being the mean direction of propagation of the x-ray beam (and more precisely the mean direction between the mean direction of propagation of the beam before and after its reflection on the optical assemblies concerned), and the sagittal direction being the horizontal transverse direction of this meridional direction (the vertical being defined by the mean normal to the part of the reflective surface of the optical assemblies which will be described and used for reflecting the incident x-ray beam). The incoming x-ray beam is after a single reflection on the optic 20 collimated in two-dimensions which are the sagittal plane (a sagittal plane being the plane defined by the sagittal direction and by the mean direction of propagation of the x-ray beam at the exit or at the entry of the concerned optical element) and in the meridional plane (the meridional plane being the plane defined by the meridional direction and the mean normal to the part of the reflective surface of the optical assemblies which will be described and used for reflecting the incident x-ray beam).

Such optical system arrangement with a collimating multilayer optic 20 arranged upstream a crystal monochromator is efficient for applications requiring a few hundred microns or a millimiter sized x-ray beam at the sample position. The X-ray spot size at the sample position as it is defined in the invention is given by the dimensions $W_s$ and $W_T$ of the beam in the two directions perpendicular to the general direction of propagation of the beam. As an indication, Ws and $W_T$ dimensions are illustrated in FIG. 2 for the x-ray beam at the exit of the two-dimensional collimating mirror 20.

However such collimating optical systems are limited for applications requiring a small spot dimension at the sample position (in the order of few hundred microns or less than 100 microns). Indeed the flux will be reduced proportionally to the surface of the spot.

Another known optical system arrangement is to use a two-dimensional focusing optic with a multilayer coating adapted upstream the crystal monochromator in order to collect the divergent x-ray beam emitted from the source and to focus such beam on a small spot at the sample. However, some intensity is lost due to the divergence of the X-ray beam incoming the monochromator in the scattering plane of the monochromator (the scattering plane of the monochromator is the plane including the incident beam and the diffracted beam) resulting from the focusing effect of the upstream multilayer optic.

FIG. 3 illustrates an optical arrangement known from state of the art where an optical element 21 with a multilayer coating collects an incident X-ray beam X1 emitted by a point source 10 and conditions such beam towards a crystal monochromator M by collimating the beam X2 in one dimension and focusing the beam X2 in the other dimension. As illustrated in FIG. 3, the x-ray beam X2 outcoming from the optical element 21 is collimated in the meridional plane of the optical element 21 corresponding to the scattering plane of the monochromator, and is focused in the sagittal plane of the optical element 21 corresponding to the sagittal plane of the Monochromator. The focusing in the sagittal plane of the Monochromator M enables to concentrate a higher intensity beam on a reduced spot size at the sample 40. This focusing effect, leading to a slightly divergent beam in the sagittal plane is possible due to a larger tolerance of the crystal monochromator in this plane (compared to the tolerance on beam divergence in the scattering plane which is the angular acceptance as shown in FIG. 1). This difference of tolerances on incident beam divergence for a crystal monochromator is referenced for example in the Document entitled "Parallel Beam Coupling into channel-cut monochromators using curved graded multilayers" from M. Schuster and H. Gobel published in J. Phys. D: Applied Physics 28 (1995) A270-275 (a maximum divergence value of 1.95° in the sagittal plane is given as an example for a Germanium(022) crystal monochromator for the Copper Kα1 line).

However, the overall usefull flux of such optical arrangement that is illustrated in FIG. 3 is limited due to a reduced divergence of the x-ray beam diffracted by the crystal in the scattering plane of the crystal monochromator. Indeed the divergence of the X-ray beam in this scattering plane of the monochromator will be limited to the reflection width of the crystal $\Delta\theta_M$ which is typically between 10 and 30 Arcseconds. As it will be illustrated later in the description of the invention, even for High Resolution X-ray Diffraction applications it can be accepted to have a higher divergence of the incidence X-ray beam that is illuminating the sample compared to the angular acceptance $\Delta\theta_M$ of a traditional crystal monochromator. However it is not possible to increase the angular acceptance of a traditional crystal monochromator while keeping a high energetic resolution.

An object of the present invention is to increase the usefull flux compared to traditional x-ray beam device for High Resolution X-ray Diffraction Applications in particular for applications requiring a small spot (in the order of few hundred microns or less than 100 microns).

A further object of the present invention is to achieve very small spot dimensions on the sample, in particular spot dimensions smaller than 50 microns for X-ray analytical applications requiring such high spatial resolution as in semiconductor metrology applications.

DESCRIPTION OF THE INVENTION

According to the invention, this object is achieved by means of an X-ray beam device for X-ray analytical applications, comprising an X-ray source designed such as to emit a divergent beam of X-rays; and an optical assembly designed such as to focus said beam onto a focal spot, wherein said optical assembly comprises a first reflecting optical element, a monochromator device and a second reflecting optical element sequentially arranged between said source and said focal spot, wherein said first optical element is designed such as to collimate said beam in two dimensions towards said monochromator device, and wherein said second optical element is designed such as to focus the beam coming from said monochromator device in two dimensions onto said focal spot.

The sample to be analyzed by means of x-ray metrology, diffraction or reflectometry can usually be located at the focal spot. Thus, the first reflecting optical element collects the divergent beam emitted by the x-ray source and, by reflection of the beam towards the monochromator device, collimates the beam in two dimensions. Typically, the beam will then have a limited divergence and will illuminate the monochromator with a limited variation of angle of incidence. The wavelength-selected beam of x-rays diffracted by the monochromator device is in turn collected by the second optical element and focused onto the sample located at the focal spot by reflection.

Due to their sequential arrangement, the first optical element can also be considered as an upstream optical element, whereas the second optical element can also be called downstream optical element.

Preferably the monochromator device comprises at least one crystal monochromator. Only those x-rays will then be able to pass the monochromator device which fulfill the well-known Bragg equation, depending on their wavelength and incidence angle with respect to particular diffracting lattice planes of the crystal. The monochromator device may also comprise two crystals placed in a so-called channel cut configuration, so that the x-ray beam diffracted by the monochromator device is parallel to, but laterally shifted with respect to the beam arriving from the first reflecting optical element. In case such a lateral shift is to be avoided, the monochromator device may even comprise four crystal monochromators arranged as two channel cuts in series, so that the x-ray beam diffracted by the monochromator device is colinear with the beam arriving from the first reflecting optical element.

In principle the first optical element and the second optical element could be simple mirror surfaces curved such as to assure the required collimation characteristics and arranged in such a way that they are hit by the incident x-ray beam under grazing incidence angles in a total reflection scheme. Advantageously, however, at least one of said first optical element and said second optical element comprises a multi-layer coating reflecting the x-ray beam according to the well known Bragg law. It allows to take advantage of an increased collecting angle for a given mirror length due to the capability of using an increased angle of incidence thus increasing the flux which arrives at the focal spot. The collecting angle can also be increased due to the capability of using larger radius of curvature resulting from the increased angle of incidence compared to total reflection mirrors.

The first optical element may have a variety of surface shapes as long as the above-discussed collimation requirement is fulfilled. Similarly, the second reflecting optical element may have a variety of surface shapes as long as the focusing requirement is fulfilled. In an advantageous embodiment of the invention, however, at least one of said first optical element and said second optical element has a reflecting surface shaped as a surface of revolution, in particular as a paraboloid of revolution. Especially an arrangement using two paraboloids is advantageous in that it allows to concentrate a maximum usefull flux on the sample with a well defined limited spot size.

In an advantageous embodiment, the reflecting surfaces of said first optical element and of said second optical element have the same reflective coating and the same radius of curvature, which facilitates their production and alignment with respect to the x-ray beam. In some applications, however, it may be preferred to use optical elements with different focal distances and in particular the focal distance of the second optical element may be selected smaller than the one of the first optical element in case a very small spot at the sample position is required. For such cases, the reflecting surfaces of said first optical element and of said second optical element will have a different radius of curvature or will be made of a different coating in order to work under a different angle of incidence.

Advantageously the x-ray source has a source size S of one hundred microns or less in order to limit the divergence of its x-ray beam and to allow obtaining a correspondingly small spot size at the sample position.

In an advantageous embodiment of the x-ray beam device according to the invention in which the source size S is correspondingly limited, the focal distance F1 of said first optical element is given by $\Delta\theta_M \leq S/F1 \leq 5*\Delta\theta_M$ in order to produce a focal spot size which is only slightly asymmetric, wherein F1 is the focal distance of said first optical element and the distance between said X-ray source and said first optical element, and wherein $\Delta\theta_M$ is the angular acceptance of said monochromator device which unit is expressed in radians in the case of this formula.

In this case, the distance F1 may be chosen such as to equal a distance F2 between the second optical element and the focal spot.

In an advantageous embodiment, the x-ray beam device according to the invention furthermore comprises a plurality of slits which are positioned between said second optical element and said focal spot and/or in front of said second optical element.

Preferably, said slits are designed and arranged at the exit or at the entry of said second optical element such as to cause an asymmetric convergence of said beam which is focused onto said focal spot, wherein the smallest convergence is at least two times the angular acceptance $\Delta\theta_M$ of the monochromator, and the largest convergence is larger than 0.25°.

In order to provide the x-ray beam device according to the invention with the required flexibility in view of different analytical applications, the slits may be adjustable in such a way as to select one among two modes of operation, one mode where the X-ray beam device is adapted for high-resolution X-ray diffraction measurements and the other mode where the X-ray beam device is adapted for reflectometry measurements or low resolution x-ray diffraction measurements.

In principle each reflecting optical element could have a completely closed surface, e.g. in the shape of a hollow truncated cone on the inside surface of which a reflecting layer is provided. This would correspond to an optical element having an opening angle of 360°. Advantageously, however, at least one of said first optical element and said second optical element has an opening angle in a range between 40° and 180°.

The x-ray beam device according to the invention may be used in various fields of research and development, from rather small laboratory x-ray applications to large-scale synchroton research devices. Typically, however, a distance between the x-ray source and the focal spot will lie in a range between 50 cm and 1.50 m.

In the above description of various embodiments it has in general been assumed that the first optical element and the second optical element are each made up of an integral optical device having a continuous reflecting surface. This is, however, not mandatory for an optical element to be used in the x-ray beam device according to the invention, and in an alternative embodiment, at least one of said first optical element and said second optical element may comprise a plurality of reflecting mirrors positioned in a Wolter arrangement.

In an advantageous embodiment of the invention, the monochromator device is made movable in such a way that it can be moved out of the X-ray beam. This movability may for example be assured by mounting the monochromator device on a translation stage which itself may be part of a goniometer that, in addition to the translation stage, can comprise one or more rotation stages.

In the following some advantageous embodiments of the x-ray beam device according to the invention will be illustrated with reference to the accompanying drawings, in which:

FIG. 5 shows a side view of an x-ray beam device according to the invention comprising two channel cut monochromators;

FIG. 6 shows a graph illustrating the lattice parameter resolution for a diffraction measurement depending on different parameters of the incident beam;

DESCRIPTION OF THE OPTICAL ELEMENTS

Figure 4:
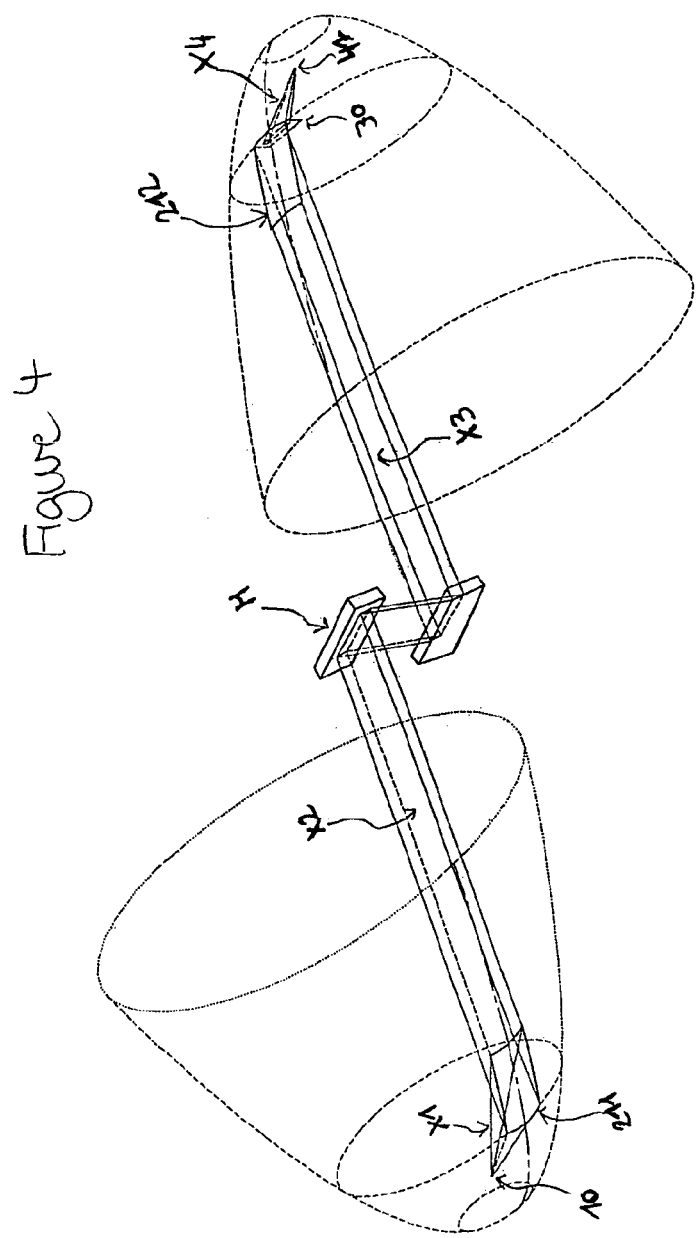
FIG. 4 shows a perspective view of an x-ray beam device according to the invention comprising a channel cut monochromator.

FIG. 4 and FIG. 5 illustrate the case where the upstream and downstream optical elements are made of single optical mirrors, and more particularly of a single reflection type.

However in some cases the optical elements are composed of two optical mirrors designed and arranged so that an incoming divergent X-ray beam on the optical element is collimated in two dimensions at the exit of such optical element. Such optical element can thus be arranged according to a Wolter design wherein a single reflection mirror whose reflective surface is shaped as an hyperboloid of revolution collects the X-ray beam emitted from a point source located at the focus of the hyperbole defining its shape and directs this beam towards a second optical mirror, whose reflective surface is shaped as a paraboloid of revolution in order to collimate the incoming beam in two dimensions. Such type of optical element will be preferred for imaging the source on a focal point with very low errors.

In another embodiment of the invention wherein each optical element of the optical assembly is composed of two mirrors, each optical system can be composed of optical mirrors curved in one dimension and arranged according to a Kirkpatrick Baez design.

In a preferred embodiment of the invention the optical elements 211 and 212 are multilayer single reflection optics with a reflective surface shaped as a toroklal, ellipsoidal or any other shape adapted such that the incident X-ray beam will be collimated after a single reflection on the optical element.

Further preferably the optical elements have a reflective surface shape describing a portion of a paraboloid of revolution as illustrated in FIG. 4. In reference to FIG. 5, each dot-dashed line is the symmetry axis of the parabola constituting the reflective surface of the respective optical element. The focus of the parabola is located on this axis at a focal distance F1 and F2, respectively for the optical element 211 and 212, from the center of the optical elements. The source 10 or the focal point 41 of the optical assembly will be placed at these focus positions.

Other two-dimensional collimating optics can be used such as a Mantel optic which is a two reflection design wherein X-rays are reflected sequentially by two mirrors curved in one dimension which are attached side by side. However in a preferred embodiment of the invention the optical elements used upstream and downstream the crystal monochromator are single reflection multilayer optics producing two-dimensional effects in order to maintain a significant intensity of the beam at the exit of the optical assembly by reducing the loss due to the reflection on the surfaces of the optical elements.

Moreover the single reflection design is more adapted to achieve a high convergence in one dimension at the exit of the optical assembly as this may be necessary for certain applications of the invention.

Figure 1:
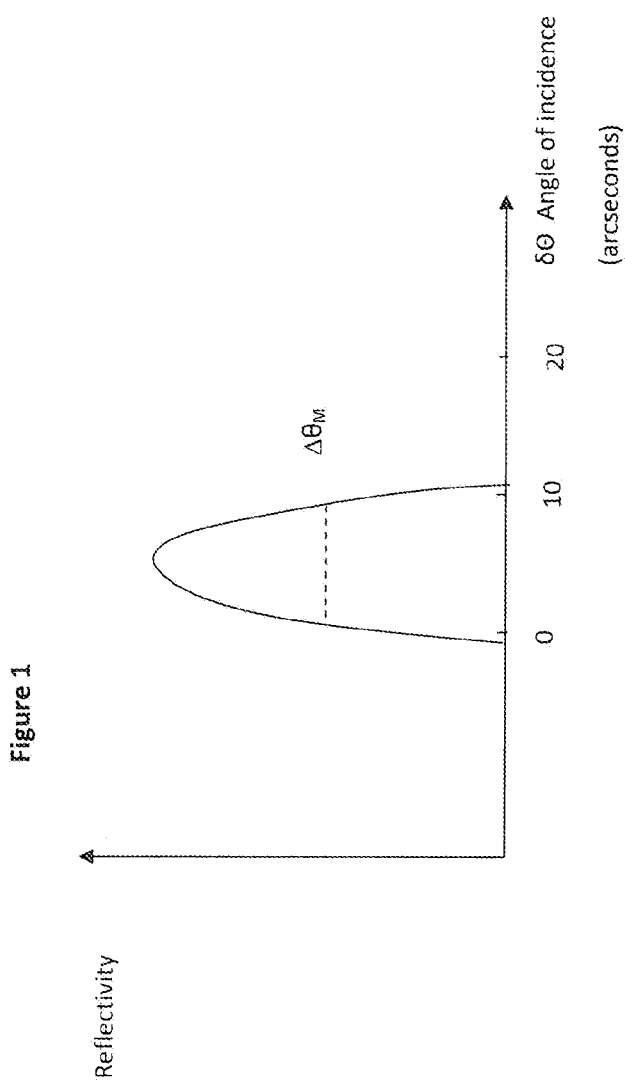
FIG. 1 illustrates a typical angular acceptance of a crystal monochromator.
Figure 2:
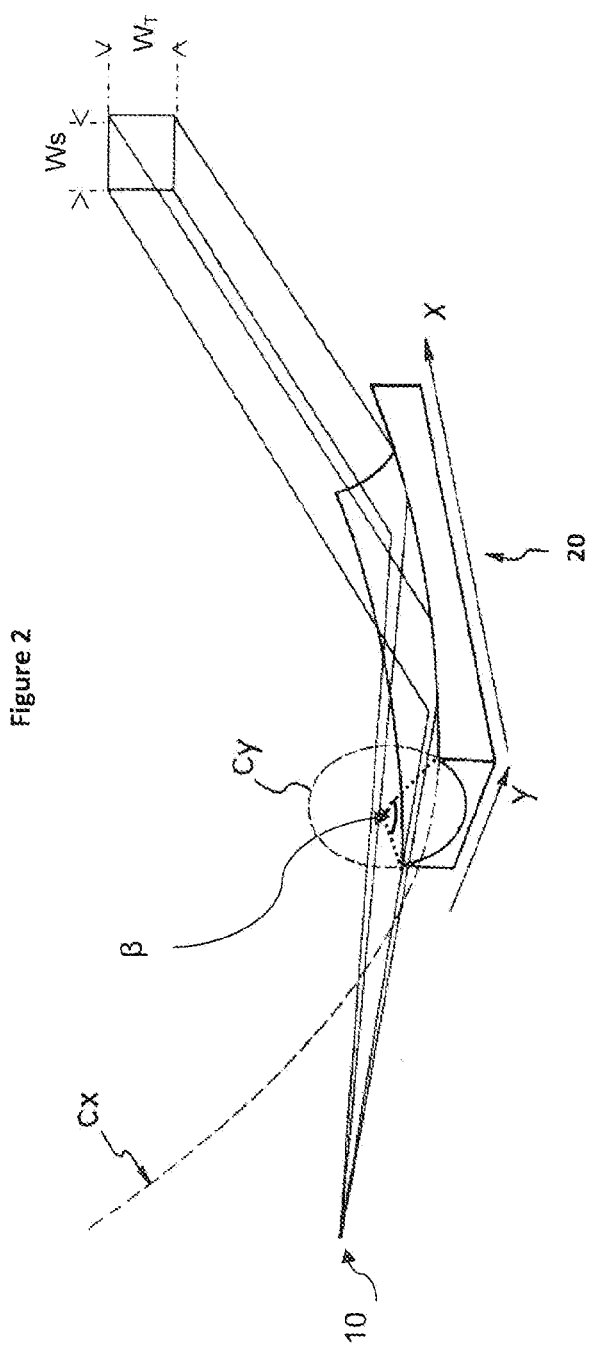
FIG. 2 is a schematic representation of a 2-dimensional collimating effect produced by a single reflection mirror.
Figure 3:
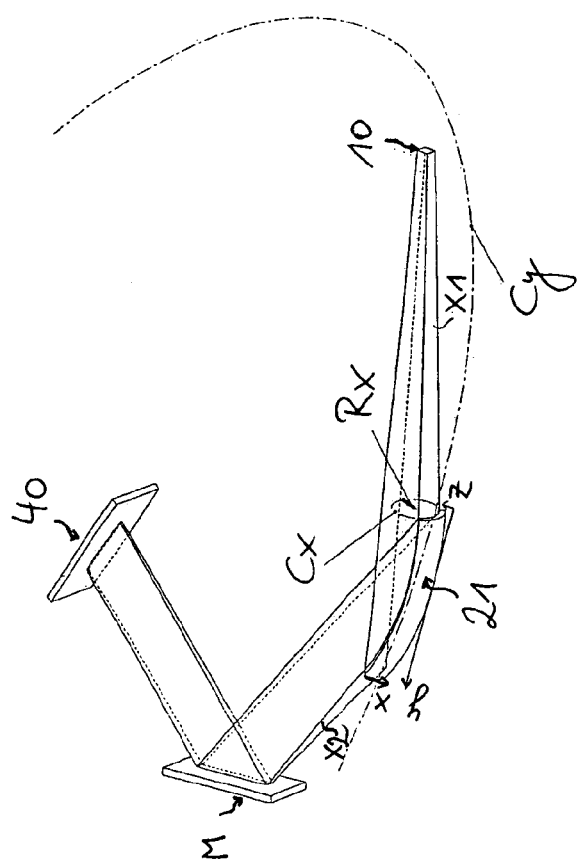
FIG. 3 illustrates the characteristics of a curved mirror collimating an x-ray beam in one dimension and focusing the beam in a further dimension towards a crystal monochromator.

In the field of application of the invention (i.e. for energies between 5 and 20 keV) the single reflection optical elements are grazing incidence optics. Due to the small focal distances required, the multilayer optical elements have a very short radius of curvature in the sagittal direction (along direction Y as defined in FIG. 2). High convergence angles can be achieved along the sagittal dimension by using a semi-revolution optic geometry. High convergence angles of few degrees can thus be achieved depending on the X-ray energy and focal distances required for the application. As opposed to the convergence angle that can be achieved along the sagittal direction, the convergence angle in the meridional direction (which is the direction X in the FIG. 2) will be limited due to the grazing incidence geometry (due to a limited length of the optical element).

In a preferred embodiment of the invention the optical assembly is producing an asymmetric convergence (asymmetry being bigger than 2 and as big as 20) at its exit. Typically the asymmetry of the convergences is defined as the ratio of the convergences of the X-ray beam outcoming from the optical assembly which are defined in the meridional and sagittal plane of the downstream optical element. The achieving of such beam property requires the use of optical multilayer elements shaped as a conic of revolution with an opening angle β which defines the revolution of the reflective surface which could be larger than 40° (a mirror with a full revolution being equivalent to an opening angle β of 360°). The opening angle β is defined in the same was as in FIG. 2. For X-ray analytical applications the opening angle β would be typically limited to 180° in order to prevent from getting X-ray spots shaped as rings on the detectors placed behind the sample to be analyzed (see FIGS. 7a and 7b which will be discussed later).

Description of the Optical Assembly

The invention will now be described in relation to FIGS. 4 and 5.

The X-ray beam device comprises an X-ray source with a point focus 10. The source can be typically a rotating anode x-ray source or a sealed tube. In a preferred embodiment of the invention the x-ray source is a high brilliance x-ray source with an effective spot size (S) of less than 100 microns, further preferably less than 50 microns. The effective spot size is the source apparent size under the typical take-off angle used to align the downstream optical elements.

The X-ray multilayer optical element 211 is designed and arranged in order to collect a portion X1 of the X-ray beam emitted by the X-ray source enclosure and to collimate such X-ray beam in two dimensions towards the monochromator device M. The X-ray Beam X2 reflected by the optical element 211 is thus rendered parallel or substantially parallel to a general direction of propagation towards a crystal monochromator device M. The reflective surface of the optical element 211 is typically made in the case of Copper X-ray radiation of a multilayer coating such as a W/Si multilayer typically made of approximately 50 stacks of W and Si bilayers, each stack having a thickness of few nanometers. Depending on the length of the mirrors, the multilayer coating may be laterally graded along the length of the mirror (direction X in FIG. 2) in order to maintain the well known bragg law over the length of the mirror.

At least one crystal monochromator achieving a very high spectral purity is arranged downstream the multilayer optical element 211. The crystal monochromator behaves as a monochromator diffracting a specific wavelength $\lambda_B$ according to Bragg law (i.e. when the incident x-ray beam impinges on the lattice planes with a Bragg angle $\theta_b$ given by: $n\lambda_B = 2d \sin \theta_B$). For example for Copper X-ray radiation a channel cut made of two crystals of Germanium could be used (where the characteristic lattice plane is 220, with a Bragg angle of 20° approximately).

The spectral acceptance of a crystal monochromator ($\Delta E_M$ for energy units or $\Delta \lambda_M$ for wavelength units) is given by the formula: $\Delta E_M/E_B = \Delta \lambda_M/\lambda_B = \cot \theta_B \, \Delta \theta_M + \delta_T$, where $\delta_T$ is the intrinsic width of the crystal reflection ($\delta_T$ is dependent on the crystal).

The optical element 211 and the crystal monochromator device M would be aligned in order to make the X-ray beam X2 having an incidence on the characteristic lattice plans of the crystal monochromators equivalent to the bragg angle for such lattice plane. The highly collimated x-ray beam X2 incoming on the crystal monochromator is diffracted with a high reflectivity near the Bragg angle $\theta_B$ over a small range of angles (this will be referred as the angular acceptance of the monochromator $\Delta \theta_M$).

In a preferred embodiment of the invention the upstream multilayer optic has a focal length F1, as illustrated in FIG. 5, such that F1/S is approximately equivalent to the angular acceptance of the crystal monochromators of the monochromator device M. This enables to collect efficiently the x-ray beam emitted by the X-ray source and to collimate it efficiently towards the monochromator. According to this embodiment of the invention, the S/F1 ratio being approximately equivalent to $\Delta \theta_M$ means that: $\Delta \theta_M \leq S/F1 \leq 5 * \Delta \theta_M$, wherein $\Delta \theta_M$ unit is expressed in radians in the case of this formula.

The crystal monochromators that will be used in the optical assembly according to the invention have an angular acceptance $\Delta \theta_M$ in the range of 10 to 30 Arcseconds (either for limiting the energetic resolution or in order to achieve a very small spot as it will be explained latter)). Consequently the source size will be typically limited to less than 100 microns (and less than 50 microns in a preferred embodiment of the invention). More over a smaller X-ray source size enables to achieve a higher brilliance x-ray source (enabling a higher electron gun power density loading on the target of the source due to better thermal evacuation conditions).

As it will be precised later the (($S/F1)/\Delta \theta_M$) ratio also defines the asymmetry of the spot size at the exit of the optical assembly and this ratio should also be selected according to this criteria.

As illustrated in FIG. 4, in the case where the monochromator device M is composed of two planar crystals (in an arrangement known as a channel cut assembly) so that the X-ray incoming beam impinges sequentially in each crystal, the axis of propagation of the beam is deviated by a value (which is typically of a few mm).

In one preferred embodiment of the invention as illustrated in FIG. 5, the monochromator is a four reflection monochromator assembly composed of two channel cut assemblies assembled so that the x-ray beam coming out of the monochromator is collinear with the incoming beam. This set-up is known as a Bartels monochromator. The use of a Bartels Monochromator will be particularly advantageous in a specific embodiment of the optical assembly wherein the optical assembly is composed of a monolithic support as it will be described later in the description of the invention.

The monochromator device M diffracts the beam X3 towards a downstream multilayer optical element 212. The Beam X3 which is substantially parallel will be collected by the downstream optical element 212 which is designed and arranged in order to focus the collimated beam X3 on a focal spot 41 located at a distance F2 from the center of the downstream optical element. A sample to be analyzed by x-ray analysis can be typically arranged at the corresponding position of the focal spot 41.

In order to adjust the convergence of the X-ray beam X4, beam blocking means 30 with a defined aperture can be arranged at the proximity of the entry and/or at the proximity of the exit of the downstream optical element 212. FIG. 4 illustrates the case wherein a plurality of linear slits are arranged at the exit of the downstream element 212 to define an asymmetric convergence of the X-ray beam X4 at the exit of the optical assembly.

FIG. 5 illustrates the case where the downstream optical element and the upstream optical element have the same orientation towards the incident beam (respectively X1 and X3) in order to deflect the incident beam in the same direction (anticlockwise in the case of FIG. 5 by a angle of $2\theta_B$ in mean, where $\theta_B$ is the bragg angle of the multilayer coatings of the two identical optical elements).

The optical assembly illustrated in FIG. 4 is different in the sense that the incident beams are defected differently (anticlockwise for optical element 211 and clockwise for optical element 212).

In a preferred embodiment of the invention, the optical elements are arranged as it is illustrated in FIG. 5 to provide a better spatial uniformity of the X-ray beam X4. Indeed in this case, the part of the x-ray beam illuminating the entry of the upstream optical element is illuminating the exit of the downstream optical element. Consequently the intensity loss due to a more intense illumination of optical elements arranged closer to the source is balanced over the entire optical assembly).

Case of an Optical Assembly with Identical Focal Distances

In a preferred embodiment of the invention, the focal distances of the optical elements F1 and F2 are identical. This will provide the advantage of having two identical multilayer optical elements (simply placed in a reverse position). Two identical optical multilayer elements will be simpler to align (same angle of incidence on each optical element) and easier to manufacture in the case where the optical assembly is made of a monolithic support as it will be described later in the description of the invention.

However in some cases different focal distances could be used (in particular when a very small spot is required, in this case F2 could be smaller than F1).

The table 1 below illustrates the beam divergence, the beam dimensions and the spectral purity after each reflection on each specific optical element of the X-ray beam. This table illustrates the case where the optical elements 211 and 212 are oriented in such manner as their meridional planes are parallel to the scattering plane of each of the crystal monochromators as illustrated in FIG. 5.

TABLE 1 x-ray beam properties after a reflection on each optics of the optical assembly in the case where the two optical elements and the crystal monochromators have two identical apertures (in the collimating side, i.e. at the exit of the upstream optical element and at the entry of the downstream optical element)

| X-ray beam properties | After the source | After Upstream optical element | After Crystal Monochromator | After Downstream optical element |
|---|---|---|---|---|
| Spot Size | $S_s \times S_T$ | Meridional plane: $\alpha_{1T} * F_1$; Sagittal plane: $\alpha_{1S} * F_1$; | Meridional plane: $\alpha_{1T} * F_1$; Sagittal plane: $\alpha_{1S} * F_1$; | Meridional plane: $\Delta\theta_M * F2$ Sagittal plane: $S_S * (F2/F1)$ |
| Divergence* | — | Meridional plane: $S_T/F1$ Sagittal plane: $S_S/F1$ | Meridional plane: Min $\{\Delta\theta_M; S_T/F1\}$ Sagittal plane: $S_S/F1$ | Meridional plane: $\alpha_{1T} * (F_1/F2)$ Sagittal plane: $\alpha_{1S} * (F1/F2)$ |
| Flux reduction | | $R_1$ | $R_m * \Delta\theta_M/(S_T/F_1)$ | R2 |

R1, R2 are the reflectivities of the mirrors, typically 60 to 90% for a multilayer mirror
*As discussed the divergence (or convergence) at the exit of the optical assembly can be adjusted by the positioning of slits close to the downstream optical element.

The X-ray beam outcoming from the monochromator device M will be at least very collimated in one dimension (in the scattering plane of each of the crystal monochromators) with a divergence limited by the angular acceptance of the crystals $\Delta\theta_M$. In the other dimension, the divergence of the beam outcoming from the monochromator device M will be depending on the divergence of the X-ray Beam X1 outcoming from the upstream optical element (which is given by $S_s/F1$).

If the focal distance F1 of the upstream optical element is sufficiently large, and the source size S is very small so that the divergence outcoming from the upstream optical element matches the angular acceptance of the crystal monochromators then the X-ray Beam X2 outcoming from the monochromator device M will have a similar divergence in both dimensions.

However depending on the constraints this condition may not be met for example in the case where a very high energetic resolution $\Delta E_B$ is required (which can only be achieved with crystals having a small angular acceptance $\Delta\theta_M$), and for applications requiring a small total distance from the source to the sample which will limit the value for F1. In this case the divergence of the beam outcoming from the monochromator device M will be asymmetric (only reduced in the scattering plane of each of the crystal monochromators).

As the incoming X-ray beam on the downstream optical multilayer element is collimated in two dimensions (however the divergence could be asymmetric) the X-ray beam will be focused in the focal point of the downstream optical element at a distance F2 from the center of the downstream optical element.

The spot size at the sample position at least in one dimension will be given by ($\Delta\theta_M$*F2), where $\Delta\theta_M$ is the angular acceptance of the crystal monochromators.

In the case where the divergence of the beam X3 arriving at the downstream optical element is asymmetric the spot size on the sample will be also asymmetric (see table 1).

The optical assembly as considered in the invention reveals very efficient for applications:
- Requiring an intense high energetic resolution x-ray beam with a $\Delta E/E < 0.1\%$ and with small spot sizes (smaller than 100 microns)
- Requiring a very small spot at least in one dimension (<50 microns)

Advantages of the Optical Assembly According to the Invention

Increased Divergence in the Scattering Plane of the Crystal Monochromator

As described in the Background Description some diffraction or analytical applications require a very low energetic resolution compatible with the bandpass of a natural crystal but would tolerate an increased convergence of the X-ray beam incoming on the sample compared to the angular acceptance of a traditional crystal monochromator.

As the x-ray beam X4 at the exit of the downstream optical element is focused on the sample according to the invention, it is possible, in a plane parallel to the scattering plane of the crystal monochromators, to adjust the convergence at the exit of the downstream optical element by putting downstream slits 30 whose aperture defines the convergence angle in this plane.

This enables to increase the usefull flux by the amount of increase in convergence in the scattering plane of the crystal monochromator compared to traditional set-up without downstream optics after the monochromator. The gain for high resolution x-ray diffraction applications will be detailed later in the description of the invention.

It is to be noted that because multilayer coatings have a high reflectivity in the field of application of the invention (between 60 to 90%), the loss due to having a design with two optical elements instead of one upstream optical element according to the state of the art, is limited.

Figure 7A:
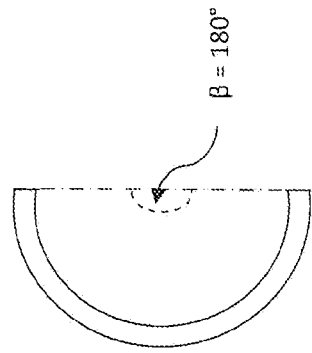
FIG. 7a and FIG. 7b show a comparison of the active surface area of a mirror in a single mirror focusing scheme (FIG. 7a) with the case of a mirror in a double paraboloid focusing scheme (FIG. 7b)
Figure 7B:
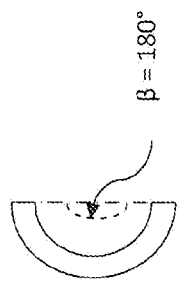

More over the optical assembly of the invention enables to produce higher flux compared to traditional focusing schemes as this is illustrated in FIG. 7a and FIG. 7b. Indeed by substituting one optical focusing element as used in the prior art (FIG. 7a) by two collimating optical elements according to the invention (FIG. 7b) it is possible to design multilayer optical elements with an increased radius of curvature along the sagittal direction of the optic (the direction Y in FIG. 2) for given focal lengths F1 and F2. FIG. 7a illustrates the active area of a single ellipsoidal multilayer mirror enabling a focusing in two dimensions for two given focal distances F1 and F2. FIG. 7b illustrates the active area of two paraboloid multilayer mirrors used in substitution of the ellipsoidal mirror and having the same focal distances F1 and F2. The design with a double paraboloid enables to increase the radius of curvature along the sagittal direction of each single optical element. This enables to achieve an increased convergence angle $\alpha_{2S}$ along the sagittal direction of the x-ray beam outcoming from a single reflection optical element.

Small Spot Advantage

The optical assembly as described hereabove enables to produce an X-ray beam wherein the spot size at the sample is controlled in one dimension by the angular acceptance of the crystal monochromator $\Delta\theta_M$. This beam property differentiates from the properties of traditional optical arrangements with one focusing optic arranged upstream a crystal monochromator wherein the spot size is given by focal distances ratio of the focusing optic and by the source size dimension.

The optical assembly according to the invention enables to achieve smaller spot size in one dimension, even smaller than the source size that is currently limited to 20 microns for sealed tube x-ray source technologies or 70 microns for rotating anode x-ray sources.

Applications of the Invention

High Resolution Diffraction Applications

The optical assembly as described in the invention is particularly adapted for high resolution x-ray diffraction applications (hereinafter referred to as HRXRD) such as
- Study of thickness, composition and stress in Epitaxial films
- Study of Superlattice structures
- Study of imperfection in single crystals As it is known in the state of the art, the angular spread (or divergence) of an incident x-ray beam and the wavelength spread of the x-ray beam (which can be referred as the energetic resolution) degrade resolution of HRXRD measurements. Both angular and wavelength spread are dependant from the Bragg angle related to the characteristic lattice parameter analysed on the sample.

According to the Bragg law, a lattice spacing $d_{hkl}$ measured by X-ray diffraction is determined by: $d_{hkl} = \lambda/2 \sin\theta$. The achievable resolution for $d_{hkl}$, which will be noted $\delta d_{hkl}$ depends on the angular spread of the incident beam (or divergence of the beam noted: $\delta\theta$) according to the following formula: $\delta d_{hkl}(\delta\theta) = (\lambda\delta\theta \cos(\theta))/(4 \sin^2\theta)$. The achievable resolution for $d_{hkl}$ depends on the wavelength spread of the incident beam (noted: $\delta\lambda$) according to the following formula: $\delta d_{hkl}(\delta\lambda) = (\delta\lambda)/2 \sin\theta$.

FIG. 6 is a graph illustrating the achievable resolution $\delta d_{hkl}$ calculated according to the formulas hereabove for two different angular spread parameters of the incident x-ray beam incoming on the sample corresponding to the angular acceptance of two different crystal monochromators (one with an angular acceptance of 10 Arcseconds and the other one with an angular acceptance of 15 Arcseconds). On the same graph the achievable resolution $\delta d_{hkl}$ for two different wavelength spread parameters of the incident x-ray beam incoming on the sample is plotted. One of the parameters, $\delta\lambda 2$, corresponds to the bandwith of a typical crystal monochromator where only the Copper Kalpha 1 line is diffracted by the monochromator, whereas the $\delta\lambda 1$ parameter corresponds approximately to the bandwith of a multilayer mirror coupled to a point focus X-ray source wherein both copper Kalpha 1 and Kalpha 2 lines are merged.

As this is illustrated in FIG. 6, for Bragg angles on the sample higher than 10°, the standard wavelength spread $\delta\lambda 2$ of traditional crystal monochromators will be the limiting factor for the achievable resolution $\delta d_{hkl}$.

As an example and as illustrated in FIG. 6, for a Bragg Angle on the sample of 20°, the tolerated divergence of the beam in the scattering plane of the sample can be more than three times larger than the angular acceptance of traditional monochromators (with $\Delta\theta_M$ in the order of 10 Arcseconds).

As described previously it is possible with the optical assembly according to the invention to achieve an increased convergence angle in the scattering plane of the monochromator. A convergence of 50 Arcseconds in the scattering plane of the monochromator can thus be achieved which will be adapted for characterizing $d_{hkl}$ parameters for sample structures having bragg angles between 20 to 30°.

In the other dimension (perpendicular to the scattering plane of the sample), the convergence of the beam incoming on the sample that is tolerated can be larger as it has a small impact on the spread of angle of incidence at the sample. A value of the order of 0.5° and as big as 1° can be tolerated.

X-Ray Reflectometry Measurements

For X-ray reflectometry measurements, a small convergence of the order of 50 millidegrees can be required in the incidence plane (the incidence plane of the sample is the plane including the incident beam and the reflected beam). Traditionally a high energetic resolution may not be required and an X-ray beam with an energy bandwith equivalent to the full Kalpha doublet (including Kalpha 1 and Kalpha 2 lines) is acceptable.

However the optical assembly as described in the invention could be efficient in the case where a very small spot is required. Indeed in the incidence plane, the X-ray beam footprint on the sample is expanded due to the grazing geometry in X-ray reflectometry measurements. With traditional focusing geometries (one focusing optic focusing the beam on the sample) the spot size $Ws \times W_T$ at the sample position will be limited by the source size (and optics error manufacturing).

It is possible with the optical assembly according to the invention to control the spot size in one dimension by choosing the angular acceptance of the monochromator which enables to achieve a smaller spot size (see table 1).

Spot sizes as small as 10 microns can be generated in one dimension over focal distances F2 of 20 cm (this clearance is necessary for example in the case of semiconductor metrology because the incidence is grazing and spot size needs to be scanned over a surface equal to half of the wafer). In reality, the spot size W' will be depending on the multilayer optical element shape error $S_e$. In the scattering plane of the crystal monochromator spot size will be approximately given by:
$W' = ((S_e)^2 + (\Delta\theta_M * F2)^2)^{1/2}$ In the other dimension, the spot size will be approximately given by the source size and the magnification ratio (F2/F1). For grazing incidence applications like X-ray reflectometry an asymmetric spot size at the sample position could be accepted (because the spot size is expanded in one dimension).

A set-up with a high brilliance X-ray source having dimensions of 30 to 100 microns and a crystal monochromator with an angular acceptance $\Delta\theta_M$ of the order of 10 Arcseconds could be effectively used to focus a monochromatic beam on a spot size of approximately 20 microns in one dimension and slightly bigger in the other dimension over focal distances F2 of 20 cm.

Application to Multi X-Ray Diffraction Analysis

The optical assembly according to the invention can also be used for low resolution X-ray diffraction applications for example for the texture analysis of polycrystalline thin films. For these applications, it can be tolerated an X-ray beam X4 illuminating the sample with a higher convergence $\alpha_2$ (a symmetric convergence of 0.2 to 0.4° for $\alpha_{2s}$ and $\alpha_{2T}$ can be accepted).

The optical assembly according to the invention can be used efficiently for multi X-ray diffraction analysis by removing the crystal monochromator depending on the type of x-ray analysis (with crystal for High Resolution X-ray Diffraction and without crystal for low resolution X-ray diffraction).

In a preferred embodiment of the invention, the crystal monochromator is a Bartels monochromator which presents the advantage of not deflecting the X-ray beam at the exit of the crystal monochromator. No further alignment of the optical elements of the optical assembly would be necessary in such case. The downstream slits 30 can be adjusted either manually or automatically in order to change the convergence $\alpha_2$ at the exit of the optical assembly as required by the change of X-ray technique.

SPECIFIC EMBODIMENT OF THE INVENTION

A specific embodiment of the invention will now be described.

In a preferred embodiment of the invention, the optical assembly according to the invention is composed of a monolithic holding support wherein the reflective surface of each optical element is directly disposed on the holding support. According to this embodiment of the invention, the reflective surface being directly disposed on the substrate means that no intermediate substrate is disposed between the support and the reflective coating.

The adhesion of the reflective surface can be achieved with an adhesive substance such as an epoxy glue or any other adhesive substance which can withstand X-rays.

In another alternative no adhesive substance is used. This will be the case if a direct deposition process such as a Physical Vapor Deposition can be done on the holding support in order to produce the reflective coating. However as the optical elements used in the optical assembly according to the invention are single reflection doubly curved X-ray mirrors with very short radius of curvature which can be smaller than 20 mm, and even smaller than 10 mm, and as high revolution angles β may be required to achieve high convergence angles, the direct deposition of thin films and in particular of multilayer coatings, which are graded multilayer coatings of few nanometers period is technically challenging (in particular because of the shadowing effect produced by the reflective surface during deposition and the variation of the coating thickness in the sagittal direction due to the sagittal curvature).

In this embodiment of the invention, the crystal monochromator can be fixed directly on the holding support on a goniometer stage which provides rotation and possibly translation degrees of freedom and which is attached to the support and located on an intermediate zone between the upstream and downstream optical elements. The rotation stage enables to align the crystal monochromator towards the incident beam in order to adjust the angle of incidence to the Bragg angle.

The crystal monochromator can also be fixed on an intermediate part physically connected to the support by a goniometer stage. The intermediate part can be a cover disposed on top of the optical assembly and attached to the holding support.

A preferred manufacturing of this optical assembly made of a monolithic support will now be described. This preferred manufacturing process enables the deposition of the reflective coating on the monolithic holding support with sufficient precision so that the optical elements do not need to be further aligned after manufacturing.

The preferred manufacturing process is a replication process from a single mandrel made of two different active areas, each active area having the shape of a conic of revolution and further preferably of a paraboloid of revolution, the paraboloids being positioned in a reverse mode along the mandrel. In a preferred embodiment of the manufacturing process the axis of revolution of the paraboloids are collinear which facilitates the manufacturing of the mandrel. In a first step the mandrel is pre-formed by an adapted technique such as diamond turning and then either super-polished or treated by a smoothening layer in order to achieve the level of microroughness required for multilayer coatings deposition.

The next step is the bonding of the coated mandrel on the holding monolithic support. The holding monolithic support can be manufactured by any adapted machining technique in order to produce the holding zones for the reflective surfaces.

The final step is the separation of the mandrel which can be done either by dissolution of a release layer placed between the mandrel and the reflective surface or by cooling the mandrel so that it shrinks more than the surrounding monolithic support.

Finally the crystal monochromator is fixed either mechanically or by an adhesive substance either directly on the holding support or on an intermediate part such as a cover of the optical assembly which is then mechanically attached to the holding support.

The invention claimed is:

1. An X-ray beam device for X-ray analytical applications, comprising:
    an X-ray source designed such as to emit a divergent beam of X-rays; and
    an optical assembly designed such as to focus said beam onto a focal spot,
wherein said optical assembly comprises a first reflecting optical element, a monochromator device and a second reflecting optical element sequentially arranged between said source and said focal spot, wherein said first optical element is designed such as to collimate said beam in two dimensions towards said monochromator device, and wherein said second optical element is designed such as to focus the beam coming from said monochromator device in two dimensions onto said focal spot;
    wherein the X-ray source has a source size S of 100 microns or less; and
    wherein the said first optical element has a focal length F1 given by $\Delta\theta_M \leq S/F1 \leq 5*\Delta\theta_M$ in order to produce a focal spot size which is only slightly asymmetric, wherein F1 is also the distance between said X-ray source and said first optical element, and wherein $\Delta\theta_M$ is the angular acceptance of said monochromator device.

2. An X-ray beam device according to claim 1, characterized in that said monochromator device comprises at least one crystal monochromator.

3. An X-ray beam device according to claim 1, characterized in that at least one of said first optical element and said second optical element comprises a multilayer.

4. An X-ray beam device according to claim 1, characterized in that at least one of said first optical element and said second optical element has a reflecting surface shaped as a surface of revolution.

5. An X-ray beam device according to claim 4, characterized in that the reflecting surfaces of said first optical element and of said second optical element have the same radius of curvature.

6. An X-ray beam device according to claim 1, characterized in that said distance F1 is equal to a distance F2 between said second optical element and said focal spot.

7. An X-ray beam device according to claim 1, characterized in that it furthermore comprises a plurality of slits, which are positioned between said second optical element and said focal spot and/or in front of said second optical element.

8. An X-ray beam device according to claim 7, characterized in that said slits are designed such as to cause an asymmetric convergence of said beam, wherein the smallest convergence is at least two times the angular acceptance $\Delta\theta_M$ of the monochromator, and the largest convergence is larger than 0.25°.

9. An X-ray beam device according to claim 7, characterized in that said slits are adjustable in such a way as to select one among two modes of operation, one mode where the X-ray beam device is adapted for high-resolution X-ray diffraction measurements and the other mode where the X-ray beam device is adapted for reflectometry measurements or low resolution x-ray diffraction measurements.

10. An X-ray beam device according to claim 1 characterized in that at least one of said first optical element and said second optical element has an opening angle in a range between 40° and 180°.

11. An X-ray beam device according to claim 1, characterized in that a distance between said X-ray source and said focal spot is in a range between 50 cm and 1.50 m.

12. An X-ray beam device according to claim 1, characterized in that at least one of said first optical element and said second optical element comprises a plurality of reflecting mirrors positioned in a VVolter arrangement.

13. An X-ray beam device according to claim 1, characterized in that the monochromator device is made removable in such a way that it can be moved out of the X-ray beam.

14. An X-ray beam device according to claim 1, characterized in that the optical assembly comprises a monolithic holding support wherein the reflective surface of each optical element is directly disposed on the holding support and the monochromator device is fixed directly on the holding support on a goniometer stage located on an intermediate zone between the upstream and downstream optical elements.

15. An X-ray beam device according to claim 1, characterized in that the optical assembly comprises a monolithic holding support wherein the reflective surface of each optical element is directly disposed on the holding support and the monochromator device is fixed on a goniometer stage on a cover of the optical assembly which is disposed on top of the optical assembly and attached to the holding support.

* * * * *